United States Patent [19]
Nack

[11] Patent Number: 5,261,817
[45] Date of Patent: Nov. 16, 1993

[54] DENTURE ADHESIVE REMOVING DEVICE

[76] Inventor: Robert L. Nack, 17 Cullen Dr., West Orange, N.J. 07052

[21] Appl. No.: 944,248

[22] Filed: Sep. 14, 1992

[51] Int. Cl.⁵ .................................. A61C 3/00
[52] U.S. Cl. ................................... 433/141
[58] Field of Search ............... 433/141, 142, 143, 144, 433/145, 146, 147

[56] References Cited
U.S. PATENT DOCUMENTS

| | | | |
|---|---|---|---|
| 1,109,924 | 9/1914 | Hoffman et al. | 433/144 |
| 1,691,786 | 11/1928 | Roth | 433/143 |
| 3,903,606 | 9/1975 | Oliver | 433/141 |
| 4,112,934 | 9/1978 | Rick | 433/142 X |
| 4,315,745 | 2/1982 | Murata | 433/141 |
| 4,781,590 | 11/1988 | Weinstein | 433/142 |
| 4,941,227 | 7/1990 | Sussman | 433/141 X |
| 5,032,082 | 7/1991 | Herrera | 433/141 |
| 5,039,302 | 8/1991 | Keys | 433/141 X |

FOREIGN PATENT DOCUMENTS 140222  12/1950  Sweden ........................ 433/141

*Primary Examiner*—Gene Mancene
*Assistant Examiner*—Nicholas D. Lucchesi

[57] ABSTRACT

A denture adhesive removing device comprising an elongated handle, affixed to the end of the handle is a thin semi-rigid scraper. Two opposing edges of the scraper are flat. One remaining edge is to be convexly shaped, approximating the shape of the palate. The other remaining edge, opposite the convexly shaped one, is concave in its approximate middle one-third and convex in each approximate outer one-third, approximating the shapes of the mandibular edentulous ridge and accompanying buccal vestibule, respectively. No sharp edges or corners are present on the scraper.

When used, the invention will efficiently and quickly remove residual denture adhesive, whether powder or cream type, from one's edentulous areas, palate, and tongue.

1 Claim, 1 Drawing Sheet

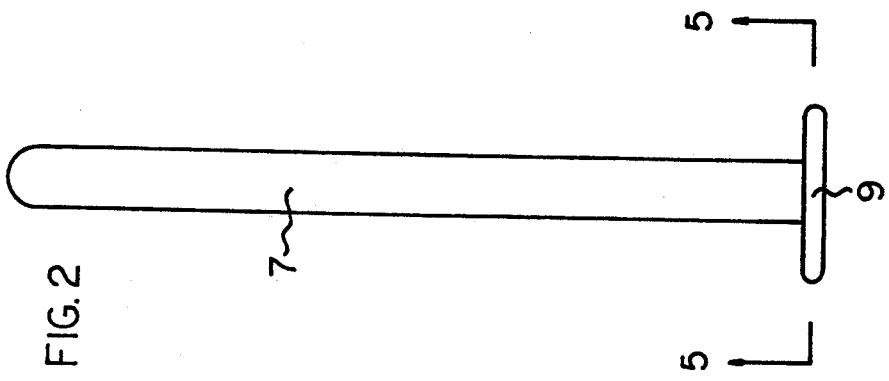
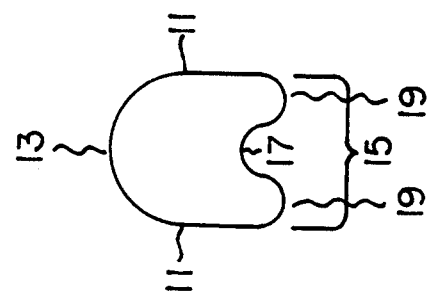
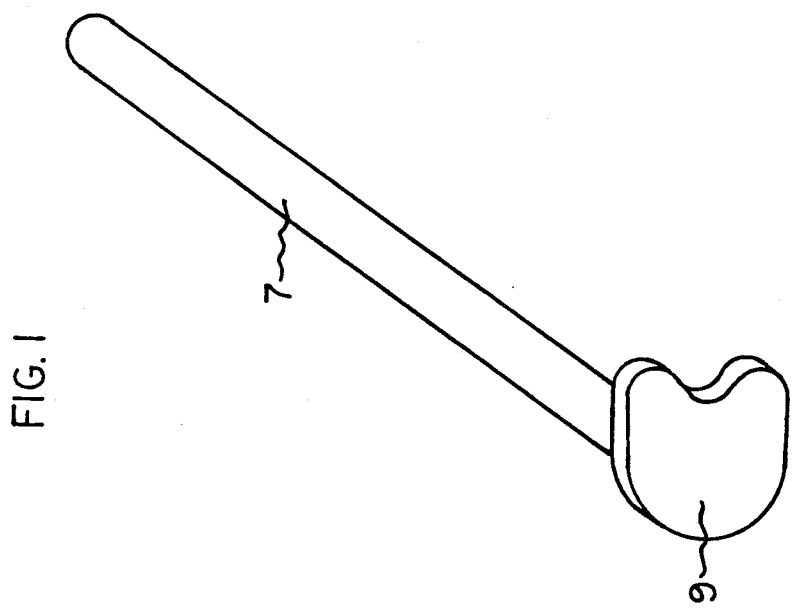

DENTURE ADHESIVE REMOVING DEVICE

BACKGROUND—FIELD OF INVENTION

This invention relates to a device, comprising a handle and scraper, with one convexly and one concavely shaped opposing sides, designed to quickly and efficiently remove any residual denture adhesive from one's edentulous areas, palate, and tongue.

BACKGROUND—DISCUSSION OF PRIOR ART

Heretofore, denture adhesive removing devices consisted generally of tissues, toilet paper, paper towels, conventional toothbrushes, and even finger nails.

More than 18 million Americans wear upper and lower full dentures. More than 26 million additional Americans wear either upper or lower full dentures or partial dentures. (Living With Your Smile, Proctor and Gamble, 1992) Many of these people use some type of denture adhesive to obtain a greater fit or tightness with a denture, to cushion the edentulous areas, and to give themselves greater stability, comfort, and confidence in wearing dentures. If someone has extremely poor fitting dentures, they should consult their dentist to determine whether or not relining or improving the fit of the old dentures, or fabricating new dentures is recommended. Denture adhesives, for those who need to or choose to use them, are placed on the tissue-bearing side of dentures. The dentures are then inserted into the mouth. Then, not only will the adhesive be in contact with the edentulous ridges and palate, but also some excess can ooze out and accumulate on the tongue.

Dentures should be removed and cleaned at least twice a day to prevent plaque buildup, stains, and reduce odors. There are a variety of denture cleansers, brushes, pastes, and rinses available to clean dentures. There are also a number of materials to soak the dentures in, usually overnight, when most dentists recommend they be left out of the mouth to rest the denture-bearing tissues. All these materials help a patient keep their dentures clean and fresh, but little, if any, attention is directed at doing the same for a denture patient's mouth. Proctor and Gamble, which makes a variety of denture cleaners and adhesives, mentions to "use a soft bristled toothbrush to brush your gums, tongue, and palate before re-inserting your dentures. This will remove plaque from your mouth, stimulate circulation, and help maintain good oral health". (Living With Your Smile, Proctor and Gamble, 1992) This is absolutely correct advice for a denture patient, and a soft bristle toothbrush is the proper device, but no mention is made in Proctor and Gamble's or in any other brochure or pamphlet that comes with a denture adhesive, how a patient should remove any residual denture adhesive from their mouth before brushing the gums, tongue, and palate.

As an active general dentist in a private group practice, I treat a large number of denture patients. In addition, for the last 11 years, I've received annual grants from Hudson County, New Jersey, to treat senior citizens residing in that county. The overwhelming majority of these patients wear dentures. The unquestioned number one complaint and concern of these patients who use denture adhesives is how to remove the adhesive from their mouths. Most are more than satisfied with the retention and comfort afforded them by the adhesives, but have enormous problems adequately removing the adhesive that remains in the mouth. This results in patients having a sticky, poor tasting, uncomfortable mouth. More important, if denture adhesive remains in the mouth, a patient cannot, with a conventional toothbrush, maintain good oral health by brushing the edentulous ridges, palate, and tongue. A surprisingly large number of denture patients, who would normally use adhesives, refuse, because of the difficulty in removing the residual adhesive from their mouths.

Most patients use the aforementioned materials, paper towels etc., to try to remove residual denture adhesive. None of these are satisfactory in removing the adhesive. In addition, some, tissues etc., tear and rip, while others, such as conventional toothbrushes, get gummed up and useless because of the buildup of adhesive on and around the bristles of the brush, which are impossible to clean.

U.S. Pat. No. 5,032,082 describes a device for removing adhesive from the palate. It is doubtful that this device can remove adhesives from the edentulous ridge areas. Also, the "lines of projections", while probably removing some denture adhesive from the palate, would simply furrow or channel most of the adhesive buildup, similar to using a rake to remove molasses from a flat surface. It is also questioned how well the device can be cleaned after use. The inventor says "the device merely requires rinsing to clean it." If this were the case, mere rinsing should remove the adhesive from a patient's mouth.

OBJECTS AND ADVANTAGES

Accordingly, it is an object of the present invention to provide a denture adhesive removing device which can efficiently remove denture adhesive from the palate, edentulous ridges, and tongue.

It is yet a further object of the present invention to provide a denture adhesive removing device which has no sharp edges or corners so that no oral mucosa can be damaged during the adhesive removal process.

It is yet a further object of the present invention to provide a denture adhesive removing device from which the adhesive can be easily removed after each use so as to maintain a hygienic device for future use.

The final object of the present invention is to provide a denture adhesive removing device which because of it's simplicity in design, can be inexpensively manufactured and thus available to denture wearers in the general public.

The device of the present invention includes an elongated handle. Affixed to said handle is a thin semi-rigid material to be used as an adhesive remover, hereafter referred to as the scraper. Said scraper is attached approximately at it's center to said handle. Two opposing sides of said scraper are to be flat. These said sides are used to scrape adhesives off the tongue. One of the two remaining sides of the scraper is to be convexly shaped, approximating the shape of the palate. Said convexly shaped side is to be used to remove adhesives from the palate. The remaining side, that opposing said convexly shaped side, is to be concavely shaped in it's approximate middle ⅓ and convexly shaped in each approximate outer ⅓ so that the convex outer ⅓'s will approximate the shape of the buccal vestibule and the concavely shaped middle ⅓ will approximate the shape of the edentulous mandibular ridge. With this design, said remaining side can be used to remove denture adhesives from both the left and right, maxillary and mandibular, edentulous ridges and buccal vestibules.

All external edges and corners, which can contact the oral mucosa, of said scraper, are to be rounded and not sharp so the oral mucosa is not damaged or injured during the adhesive removal process.

The aforementioned two sides with convexities and concavities can be manufactured with varying degrees of convexity and concavity to accomodate denture patients with flat palates to those with high or vaulted palates. The same manufacturing variations can be applied to accomodate flat mandibular ridges or high rounded ridges or wide ridges, etc. If I tell a denture patient he has a high or vaulted palate and a flat mandibular ridge, he could purchase the appropriately sized denture adhesive removing device. If said variations in the manufacturing process are not feasible, a standard device could be fabricated in which the concavities and convexities approximate the "average" palate and edentulous ridge. With said standard device, simple manipulation of the device while in use, would efficiently remove adhesives from any shaped palate, edentulous ridge, or buccal vestibule.

The handle of the invention could be made from plastic, such as that used for a conventional toothbrush handle. The scraper could be made from the same or possibly a less rigid material. In any event, a tissue, paper towel, or the like will easily remove the adhesive from said scraper, maintaining a clean, hygienic device. Removing the adhesive from said scraper with a paper towel, etc., is done easier than removing the adhesive from the mouth with a paper towel, etc., because the adhesive is much more accessible on said scraper than in the mouth. In addition, saliva in the mouth contributes to the weakening and subsequent tearing of the paper towel, etc., while this problem does not exist on said scraper. Many denture patients complain of excessive saliva as a result of wearing dentures. This complicates the removal of denture adhesives from the mouth with paper products.

The handle of the invention should be made so that its dimensions lend itself to be stored in a conventional toothbrush holder when not in use.

The simplicity of the design and the proposed materials involved in the manufacturing of the present invention should make it inexpensive, and thus available to all denture wearers in the general public.

Readers will find further objects and advantages of the invention from a consideration of the ensuing description and the accompanying drawings.

BRIEF DESCRIPTION OF THE DRAWINGS

In the drawings:

FIG. 1 is a perspective view of the Denture Adhesive Removing Device.

FIG. 2 is a top plan view of the present invention of FIG. 1.

FIG. 3 is a transverse sectional view taken along the line 5,5 of FIG. 1.

DETAILED DESCRIPTION OF THE PREFERRED EMBODIMENT

Referring to FIG. 1 in detail, the perspective view of the Denture Adhesive Removing Device, the handle 7, is shown, to which at one end is affixed, approximately at it's center, the semi-rigid scraper 9.

Referring to FIG. 3, the transverse sectional view taken along the line 5,5 of FIG. 2, the adhesive removing components of said scraper 9, are shown in detail. Two opposing sides 11, of the scraper 9 are flat. A third side 13, is convexly shaped, approximating the shape of the palate. The remaining fourth side 15, that opposing said third side 13, is concavely shaped in its approximate middle ⅓, 17, and convexly shaped in each outer approximate ⅓, 19. On said remaining fourth side 15, said middle ⅓ concavity 17, approximates the endentulous mandibular ridge. Each outer ⅓ convexity 19, approximates the buccal vestibule. It's important to note on FIGS. 1, 2 and 3, that no external edges or corners, which can contact the oral mucosa, are sharp and therefore injurious to said tissue.

Operation of Invention

In operation, the Denture Adhesive Removing Device is grasped, in either the right or left hand, by the handle 7. Obviously, the user's dentures are not in his/her mouth at this time. The device is inserted in the mouth with said convex third side 13, facing superiorly, or towards the palate. The device, with said third side 13 now positioned as far posteriorly as possible to the junction between the hard and soft palates, is then pressed superiorly, and as said third side 13, remains in contact with the palate, is pulled by the handle 7, anteriorly to remove and accumulate on the scraper 9, residual denture adhesive from the palate. The device is then removed from the mouth and the adhesive on the scraper 9, is removed with a paper towel, tissue, etc. This procedure is duplicated as much as necessary to remove all residual denture adhesive from the palate.

The device, after the palate is clean, is reinserted in the mouth, as before. Now, however, the device is pressed inferiorly so that the concave middle ⅓, 17, of said remaining fourth side 15, is in contact with the edentulous mandibular ridge as far posteriorly as possible. The device is then pulled anteriorly, remaining in contact with the mandibular ridge, so that residual denture adhesive is removed not only from the edentulous mandibular ridge, but also from the buccal vestibule and the floor of the mouth adjacent to the edentulous ridge by said outer convex ⅓'s, 19.

The device is designed such that one single convex outer ⅓, 19, which removes denture adhesive from the buccal vestibule on the mandibular left side, will remove adhesive from the floor of the mouth area adjacent to the ridge on the mandibular right side. This is due to the fact that the device is always pulled anteriorly and then taken out of the mouth to have the removed adhesive taken off the scraper 9.

The device can now be turned and inserted into the oral cavity, so that the remaining fourth side 15, is facing superiorly. Now, as was done with the edentulous mandibular ridge, the present invention can be used, with the concave middle ⅓, 17, of said remaining fourth side 15, opposing the maxillary edentulous ridge. In this case, one of the outer convex ⅓'s, 19, will be in the maxillary buccal vestibule. This positioning will serve to remove denture adhesive from the left and right maxillary edentulous ridges and accompanying buccal vestibules. As before, the device should be moved in a posterior to anterior direction to remove the residual adhesive. Also, as before, tissues, paper towels, etc., can be used to remove the adhesive from the scraper 9.

The opposing flat sides 11, are used to remove any residual denture adhesive from the tongue. Said sides 11, will accomplish this by inserting the device in the mouth as far posteriorly as possible. The device is then pulled anteriorly, while either of the said sides 11, is against the dorsal surface of the tongue. Removal of the denture adhesive from said sides 11, is accomplished as before, with tissues, paper towels, etc.

The present invention, since it can be cleaned easily with paper towels, etc., and then rinsed, can be stored hygienically, as would a standard toothbrush, in a conventional toothbrush holder, when not in use.

Thus the reader will see that the Denture Adhesive Removing Device provides an efficient, quick, and economical means to remove residual denture adhesive from the palate, edentulous areas, and tongue.

Although the present invention has been described in connection with a preferred embodiment, it is to be understood that one skilled in the art can suggest changes in form, construction, and materials, which would nevertheless, come within the scope of the following claims.

I claim:

1. A denture adhesive removing device, comprising: a thin, semi-rigid scraper including a substantially planar member having front-facing and rear-facing surfaces, said member bounded by a continuous outer edge, said edge having opposing first and second substantially linear portions, opposing third and fourth portions, said third portion having a convex shape which conforms to the shape of a patients' palate, said fourth portion having first and second end sections with a middle section therebetween, said end sections each having a substantially convex shape conforming to the shape of the buccal vestibule of said patient, said middle section having a substantially concave shape conforming to the shape of the edentulous mandibular ridge of said patient, wherein said outer edge has rounded corners and is free of sharp portions which may damage tissue within the mouth of said patient; and a handle portion having first and second end portions, said handle portion being affixed at one of said end portions to said front-facing surface of said member at a distance from said outer edge, said handle portion extending substantially perpendicular to said member.

* * * * *